(12) United States Patent
Bosch Cartés et al.

(10) Patent No.: US 7,612,219 B2
(45) Date of Patent: Nov. 3, 2009

(54) 11—[ (Z) -3- (DIMETHYLAMINO) PROPYLIDENE]—6, 11-DIHYDRO-DIBENZ [B,E] OXEPIN-2-YI ]—ACETIC ACID

(75) Inventors: Joan Bosch Cartés, Barcelona (ES); Jordi Bachs Roca, Barcelona (ES); Antonia Ma Gomez Gomez, Barcelona (ES); Yolanda Alonso Marin, Barcelona (ES); Mercè Bessa Sanchez, Barcelona (ES)

(73) Assignee: Urquima S.A., Palau Solita i Plegamans (ES)

( * ) Notice: Subject to any disclaimer, the term of this patent is extended or adjusted under 35 U.S.C. 154(b) by 251 days.

(21) Appl. No.: 11/658,600

(22) PCT Filed: Jul. 11, 2005

(86) PCT No.: PCT/EP2005/007501

§ 371 (c)(1),
(2), (4) Date: Jan. 26, 2007

(87) PCT Pub. No.: WO2006/010459

PCT Pub. Date: Feb. 2, 2006

(65) Prior Publication Data

US 2009/0005579 A1    Jan. 1, 2009

(30) Foreign Application Priority Data

Jul. 28, 2004    (ES)    ................. 200401864

(51) Int. Cl.
*C07D 313/12*    (2006.01)
*A61K 31/335*    (2006.01)

(52) U.S. Cl. ....................... 549/355; 514/450

(58) Field of Classification Search ................. 514/450; 549/355

See application file for complete search history.

(56) References Cited

U.S. PATENT DOCUMENTS

| | | | |
|---|---|---|---|
| 4,871,865 A | 10/1989 | Lever, Jr. et al. | |
| 5,116,863 A | 5/1992 | Oshima et al. | |
| 6,638,977 B1 * | 10/2003 | Madison et al. | ............. 514/538 |

OTHER PUBLICATIONS

Etsuo, Otaki et. al. "Synthesis and antiallergic activity of 11-(aminoalkylidene)-6,11-dihydrodibenz[b,e]oxepin derivatives." Journal of Medicinal Chemistry, 1992 35(11), 2074-84.*
Soederberg, Bjoern et. al. "Synthesis of fused indoles by sequential palladium-catalyzed Heck reaction and N-heteroannulation." Tetrahedron, 2005, 61(15), 3637-3649.*
Denieul, Marie-Pierre et. al. "Synthesis of the Benzophenone Fragment of Balanol via an Intramolecular Cyclization Event." Journal of Organic Chemistry, 2000, 65(19), 6052-6060.*

Finch, Harry, et al., "The Synthesis of a Conformationally Restrained, Combined Thromboxane Antagonist/Synthase Inhibitor Using an Intramolecular 'Stille'-or 'Grigg'-Palladium-Catalysed Cyclisation Strategy," Tetrahedron Letters, 34(51): 8353-8356 (1993).
Chaudhuri, Gopeswar et al., "A highly regio- and stereoselective synthesis of (Z)-3-arylidene-2,3-dihydro-5H-1,4- benzodioxepin-5-ones and (Z)-3-arylidene-1,2,3,5-tetrahydro-4,1-benzoxazepin-5-ones through palladium-copper catalysis," J. Chem. Soc. Perkin Trans. 1: 775-779 (2000).

* cited by examiner

*Primary Examiner*—Rita J Desai
*Assistant Examiner*—David K O'Dell
(74) *Attorney, Agent, or Firm*—Rothwell, Figg, Ernst & Manbeck

(57) ABSTRACT

Process for the preparation of olopatadine (I), which comprises reacting a compound of formula (V) in the presence of a palladium catalyst to provide a compound of formula (VI), wherein the acid protecting group is removed to provide the compound of formula (I) and if desired, transformation into its salts.

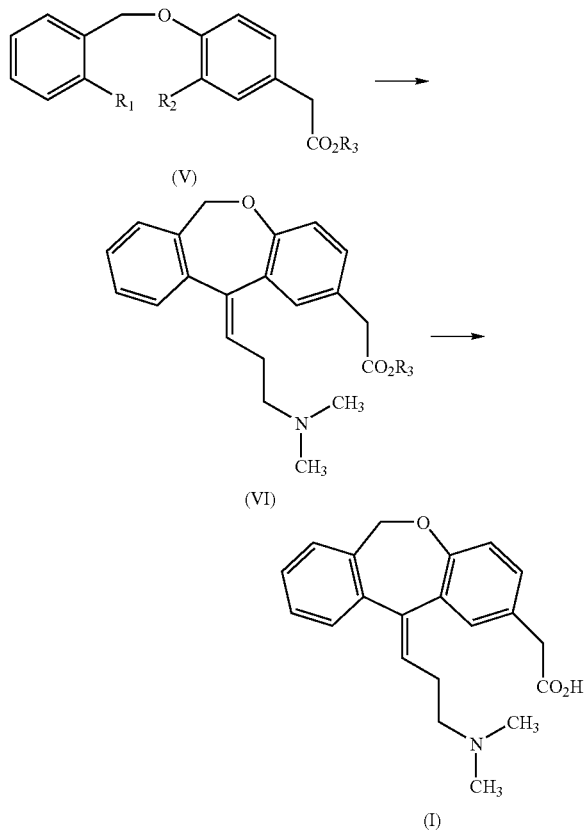

20 Claims, No Drawings

11—[ (Z) -3- (DIMETHYLAMINO) PROPYLIDENE]—6, 11-DIHYDRO-DIBENZ [B,E] OXEPIN-2-YI ]—ACETIC ACID

This application is a 371 filing of PCT/EP2005/007501, filed Jul. 11, 2005 which claims priority to Spanish Application No. 200401864, filed Jul. 28, 2004. These prior applications are incorporated herein by reference.

The present invention provides a new process for the preparation of 11-[(Z)-3-(dimethylamino)propylidene]-6,11-dihydro-dibenz[b,e]oxepin-2-yl]-acetic acid useful as an antihistaminic agent, and its intermediates of the synthesis.

DESCRIPTION OF THE TECHNICAL STATUS

The compound of 11-[(Z)-3-(dimethylamino)propylidene]-6,11-dihydro-dibenz[b,e]oxepin-2-yl]-acetic acid represented by formula I, commonly known as Olopatadine, has been used as an active constituent drug, in form of its hydrochloride salt.

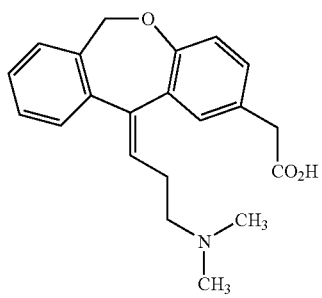

I

The preparation of the compound of formula I has been described previously in U.S. Pat. Nos. 5,115,883 and 4,871,865, where it is prepared from the basic structure dibenzo[b,e]oxepine-11-one (formula II) suitably substituted,

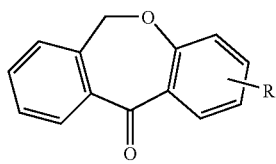

II where R is $CH_2COOH$ or a precursor group of $CH_2COOH$, such as halogen or $CH_2CN$. This transformation is carried out by means of two different synthetic pathways:

A/ Preparation of compound of formula I by means of a Wittig reaction by reacting a compound of formula II with the triphenylphosphonium salt of formula III.

$Ph_3P=CH(CH_2)_2N(CH_3)_2$      (III)

B/ Alternatively, the compound of formula I may be prepared by means of a Grignard reaction, reacting compounds of formula II with the reagent of formula IV,

$(CH_3)_2NCH_2CH_2CH_2MgX$      (IV)

where X is halogen, followed by dehydration with a strong acid.

Until now, all processes described for the preparation of olopatadine have some disadvantages for their application at industrial scale. For this reason, it is necessary to find an alternative process for the preparation of olopatadine and/or its pharmaceutically acceptable salts, which is suitable for the preparation at industrial scale. This problem is solved by the new preparation process claimed in this patent.

SUMMARY OF THE INVENTION

One aspect of the present invention relates to the process of the preparation of 11-[(Z)-3-(dimethylamino)propylidene]-6,11-dihydro-dibenz[b,e]oxepin-2-yl]-acetic acid of formula I and/or its salts,

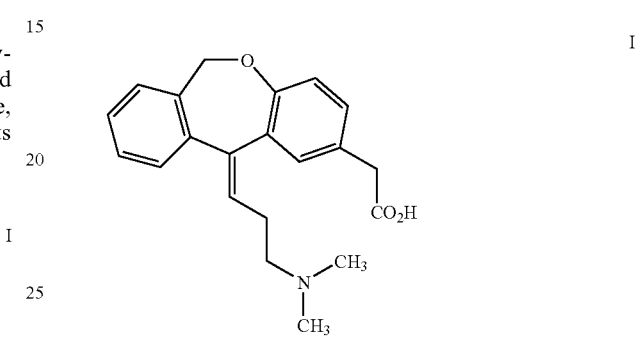

I comprising reacting the compound of formula V,

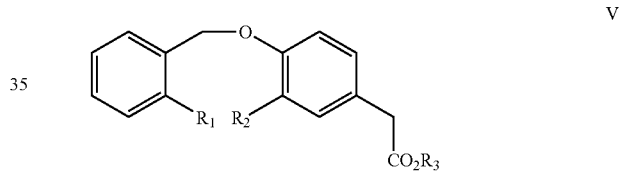

V wherein one of $R_1$ and $R_2$ is halogen and the other is $CH=CH-CH_2-CH_2-N(CH_3)_2$ and $R_3$ is an acid protecting group, in the presence of a palladium catalyst, to provide a compound of formula VI,

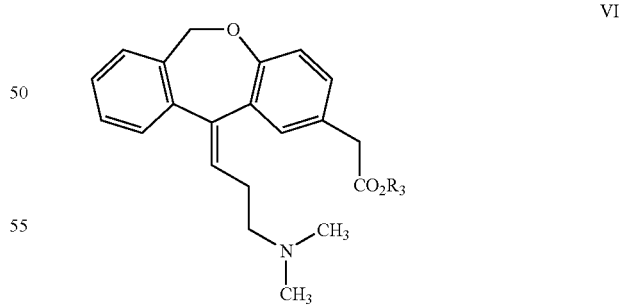

VI wherein the acid protection group is removed to provide the compound of formula I and if desired, transformation into its salts.

Another aspect of the present invention is a process for the preparation of 11-[(Z)-3-(dimethylamino)propylidene]-6,11-dihydro-dibenz[b,e]oxepin-2-yl acetic acid of formula I and/or its pharmaceutically acceptable salts,

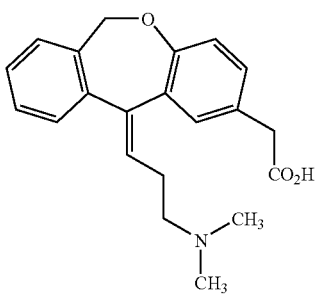

comprising reacting compounds of formula IX

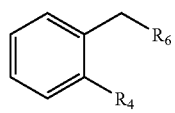 IX with compounds of formula X,

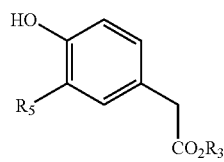 X wherein $R_6$ is a leaving group and one of $R_4$ and $R_5$ is halogen and the other is CHO and $R_3$ is as defined above, in the presence of a base to obtain compounds of formula VII,

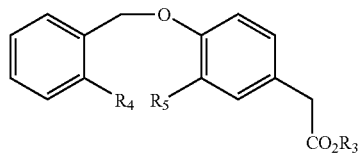 VII wherein $R_4$ is as defined for formula IX and $R_5$ and $R_3$ are as defined for formula X, reacting compounds of formula VII with compounds of formula VIII or a salt thereof,

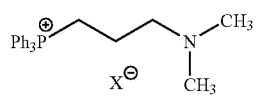 VIII wherein X is iodine, chlorine or bromine, in the presence of a base to obtain compounds of formula V

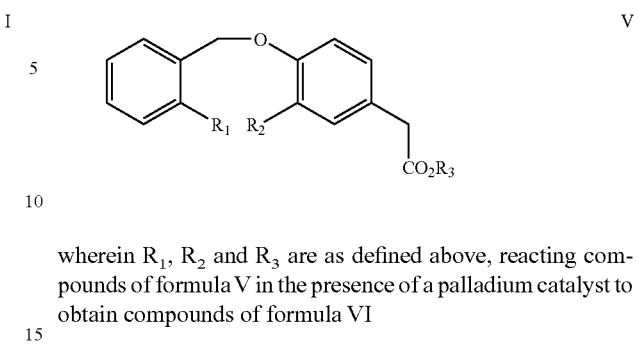

wherein $R_1$, $R_2$ and $R_3$ are as defined above, reacting compounds of formula V in the presence of a palladium catalyst to obtain compounds of formula VI

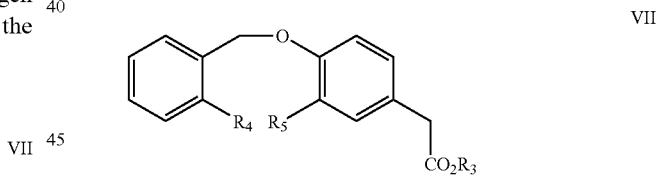 VI and removing the acid protecting group $R_3$ of compounds of formula VI to obtain a compound of formula I; and if desired, converting the compound of formula I into its pharmaceutically acceptable salts.

Another aspect of the present invention are the compounds of formula VII,

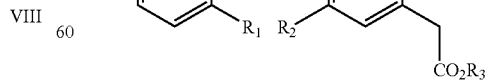 VII wherein one of $R_4$ and $R_5$ is halogen and the other is CHO and $R_3$ is an acid protecting group.

Another aspect of the present invention are compounds of formula V,

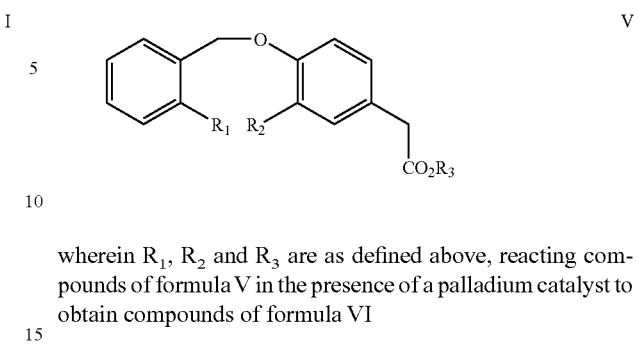 V wherein one of $R_1$ and $R_2$ is halogen and the other is $CH{=}CH{-}CH_2{-}CH_2{-}N(CH_3)_2$ and $R_3$ is an acid protecting group.

Compounds of formula VII and V are useful as intermediates in the preparation of a compound of formula I.

DESCRIPTION OF THE INVENTION

Within the definitions that are mentioned, the term leaving group means a group that removes during a removal reaction, such as halogen, for example iodine, chlorine or bromine or an alkylsulphonyloxy or arylsulphonyloxy group, for example methansulphonyl, toluenesulphonyl, trifluoromethansulphonyl or benzenesulphonyl.

Acid protecting group is a term used for any group described in the literature for this purpose, such as $C_1$-$C_4$ alkyl, $C_1$-$C_4$ haloalkyl, $C_1$-$C_4$ alkoxy-$C_1$-$C_4$-alkyl, aryl-$C_1$-$C_4$-alkyl, $C_3$-$C_6$ cycloalkyl or aryl, wherein aryl is phenyl or phenyl substituted by one or more groups such as, $C_1$-$C_4$ alkyl, halogen, $C_1$-$C_4$ haloalkyl, $C_1$-$C_4$ alkoxy or $C_1$-$C_4$ haloalkoxy. Preferably the acid protecting group is $C_1$-$C_4$ alkyl, and even more preferably it is methyl.

The term halogen, as a group or part of a group, means iodine, chlorine or bromine, preferably iodine.

The term $C_1$-$C_4$ alkyl, as a group or part of a group, means a linear or branched chain of 1 to 4 carbon atoms, for example methyl, ethyl, propyl, isopropyl, butyl, isobutyl, sec-butyl, and tert-butyl.

The meaning of a group $C_1$-$C_4$ haloalkyl is a group resulting from the substitution of one or more hydrogen atoms of a $C_1$-$C_4$ alkyl by one or more halogen atoms (that is fluorine, chlorine, bromine or iodine), which may be the same or different. For example trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2,3,3,3-pentafluoropropyl, heptafluoropropyl, 4-chlorobutyl, 4-fluorobutyl, 4-iodobutyl and 4-bromobutyl.

Examples for $C_3$-$C_6$ cycloalkyl are cyclopropyl, cyclobutyl, cyclopentyl or cyclohexyl.

Examples for $C_1$-$C_4$ alkoxy are methoxy, ethoxy, propoxy, isopropoxy, butoxy, isobutoxy, sec-butoxy and tert-butoxy.

The meaning of a group $C_1$-$C_4$ haloalkoxy is a group resulting from the substitution of one or more hydrogen atoms of $C_1$-$C_4$ alkoxy by one or more halogen atoms, which may be the same or different. For example trifluoromethoxy, fluoromethoxy, 2-chloroethoxy, 2-fluoroethoxy, 2-iodoethoxy, 2,2-difluoroethoxy, 2,2,2-trifluoroethoxy, pentafluoroethoxy, 3-fluoropropoxy, 3-chloropropoxy, 2,2,3,3-tetrafluoropropoxy, 2,2,3,3,3-pentafluoropropoxy, heptafluoropropoxy, 4-fluorobutoxy and 4-chlorobutoxy.

The meaning of a group $C_1$-$C_4$ alkoxy-$C_1$-$C_4$-alkyl is a group resulting from the substitution by one or more hydrogen atoms of $C_1$-$C_4$-alkyl for one or more $C_1$-$C_4$-alkoxy, which may be the same or different. For example, metoxymethyl, 1-metoxyethyl, 2-methoxyethyl, 1-methoxypropyl, 2-methoxypropyl, ethoxymethyl, 1-ethoxyethyl, 2-ethoxyethyl, 2-propoxyethyl, isopropoxymethyl, 2-isopropoxyethyl, butoxymethyl, 1-butoxyethyl, 2-butoxyethyl and sec-butoxymethyl, 2-sec-butoxyethyl, tert-butoxymethyl, 2-tert-butoxyethyl and 1-tert-butoxyethyl.

The meaning of a group aryl-$C_1$-$C_4$-alkyl is a group resulting from the substitution by one or more hydrogen atoms of $C_1$-$C_4$-alkyl for one or more aryl groups, which may be the same or different, such as, phenyl-methyl, phenyl-ethyl, 1,1-diphenylethyl, 1,2-diphenylethyl, 1-phenylpropyl, 4-bromophenylisopropyl, 4-bromophenylmethyl, 4-chlorophenylethyl, 4-methoxyphenylmethyl, 4-bromophenylethyl, 1-(4-bromophenyl)propyl and 2-(4-bromophenyl)propyl, The process for the preparation of the compound of formula I, one of the objects of this invention can preferably be summarized in the following diagram:

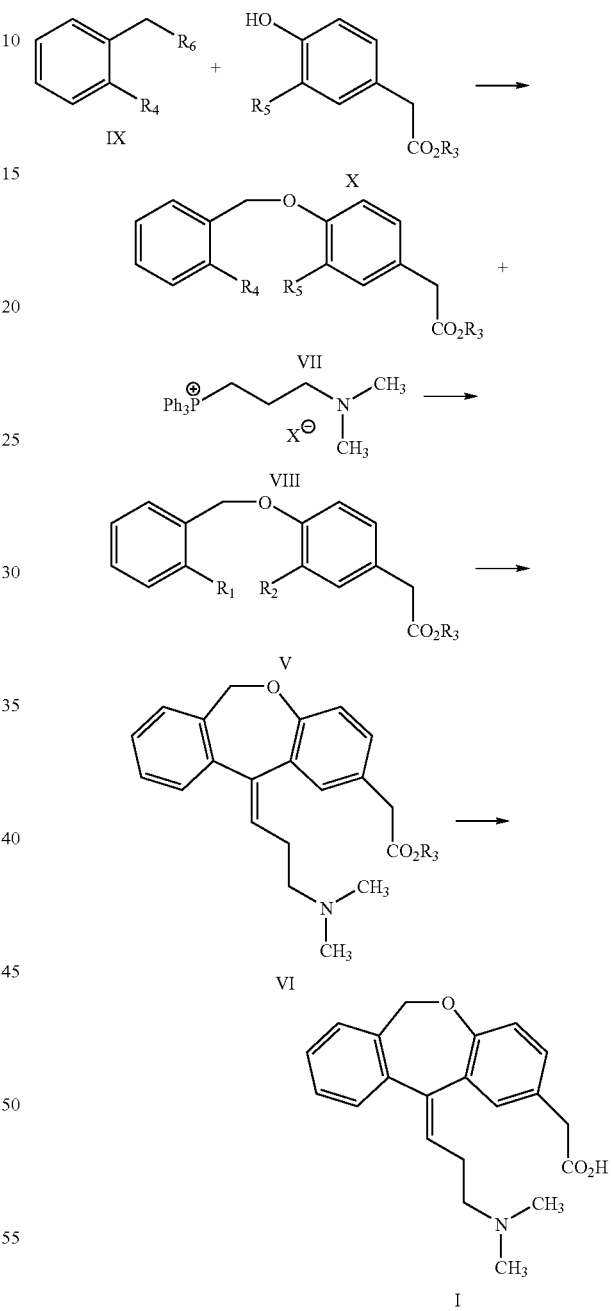

The transformation of compounds of formula V into compounds of formula VI is carried out in the presence of a palladium catalyst, such as any standard catalyst well known in organic synthesis, for example palladium tetrakis(triphenylphosphine) palladium or palladium acetate (the latter being preferred), and optionally in the presence of a phosphine such as triphenylphosphine or tri-O-tolylphosphine and/or a base, such as triethylamine, tetrabutylammonium chloride or a alkaline metal carbonate, for example potassium carbonate or sodium carbonate, with a suitable solvent, such as acetonitrile, dimethylformamide, water or mixtures thereof and at a suitable temperature preferably comprised between room temperature and the reflux temperature of the solvent, more preferably the temperature range is around 60-75° C.

In a preferred embodiment of the transformation process of compounds of formula V into compounds of formula VI, $R_3$ is $C_1$-$C_4$-alkyl.

In a preferred embodiment of the transformation process of compounds of formula V into compounds of formula VI, $R_1$ is halogen and $R_2$ is (E)-CH=CH—$CH_2$—$CH_2$—$N(CH_3)_2$.

In a preferred embodiment of the transformation process of compounds of formula V into compounds of formula VI, $R_1$ is (Z)-CH=$CH_2$—$CH_2$—$N(CH_3)_2$ and $R_2$ is halogen.

In a preferred embodiment of the process, the transformation of compounds of formula V into compounds of formula VI is preferably carried out using palladium acetate as a palladium catalyst, in the presence of a base, preferably potassium carbonate and tetrabutylammonium chloride in acetonitrile-water.

The acid protecting group of compounds of formula VI is removed thus obtaining the compound of formula I, by using standard conditions for removing acid protecting groups well known to those skilled in the art, for example following the process described in Protective groups in Organic synthesis by Theodora W. Greene (John Wiley and sons, Inc). Preferably wherein $R_3$ is a $C_1$-$C_4$-alkyl, the removal is carried out in an alkaline medium such as aqueous NaOH and wherein $R_3$ is an aryl-$C_1$-$C_4$-alkyl the removal is carried out by catalytical hydrogenation.

If desired, optionally the compund of formula I can be converted into its pharmaceutically acceptable salts, such as salts prepared with inorganic acids, for example HCl, Hl and salts prepared with organic acids such as, methansulfonic acid, trifluoromethansulfonic acid, fumaric acid or oxalic acid, preferably its hydrochloride salt. These salts are prepared by the reaction of compound of formula I with the appropiate acid, in a suitable solvent and at a temperature preferably comprised between room temperature and the reflux temperature of the solvent, more preferably the temperature is room temperature (considered around 15-30° C.).

Compounds of formula V can be prepared from compounds of formula VII,

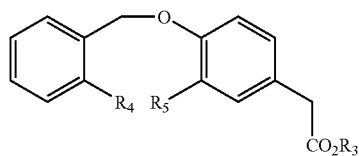

VII wherein one of $R_4$ and $R_5$ is halogen and the other is CHO and $R_3$ is as defined above, by reaction with compounds of formula VIII or a salt thereof,

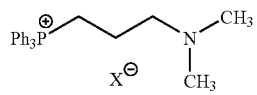

VIII wherein X is iodine, chlorine or bromine, in the presence of a base.

The transformation of compounds VII into compounds of formula V is carried out by reaction of compounds of formula VIII or a salt of acid addition, such as HCl, HBr o Hl , preferably Hl , in the presence of a base, preferably a lithium base or a sodium base, for example butyl lithium, lithium diisopropylamide, sodium hydride, potassium hydride, sodium carbonate, potassium carbonate, sodium bis(trimethylsilyl)amide, potassium bis(trimethylsilyl)amide or lithium bis(trimethylsilyl)amide, preferably in a suitable solvent, such as toluene or tetrahydrofurane, preferably in an atmosphere of inert gas such as nitrogen or argon and at a suitable temperature, preferably room temperature.

In a preferred embodiment of the process, X is iodine.

In another preferred embodiment of the process, one of $R_4$ and $R_5$ is iodine and the other is CHO.

In a more preferred embodiment, in the conversion of compounds of formula VII into compounds of formula V, $R_4$ is iodine and $R_5$ is CHO and the reaction is carried out with a lithium base such as butyl lithium, diisopropyl lithium or lithium bis(trimethylsilyl)amide, preferably lithium bis(trimethylsilyl)amide.

In another more preferred embodiment, in the conversion of compounds of formula VII into V, $R_4$ is CHO and $R_5$ is iodine and the reaction is carried out with a sodium base such as sodium hydride, sodium carbonate or sodium bis(trimethylsilyl)amide, preferably sodium bis(trimethylsilyl)amide.

Compounds of formula VII may be prepared from compounds of formula IX

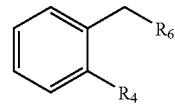

IX by reaction with compounds of formula X

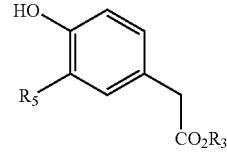

X wherein $R_6$ is a leaving group and $R_3$, $R_4$ and $R_5$ are as defined above, in the presence of a base.

The base used in the preparation of compounds of formula VII may be for example, sodium carbonate, potassium carbonate, sodium hydrogen carbonate, potassium hydrogen carbonate or potassium fluoride, preferably potassium carbonate, and preferably the reaction is carried out in a suitable solvent, such as acetone, acetonitrile or N,N-dimethylformamide, preferably acetonitrile, at a temperature preferably between room temperature and reflux temperature, more preferably the temperature is reflux temperature of the solvent.

In a preferred embodiment, $R_6$ is halogen.

In a more preferred embodiment, $R_6$ is chlorine, bromine or iodine.

Compounds of formula V and VII are new and are another embodiment of the invention as mentioned above.

A preferred embodiment are compounds of formula VII, wherein one of $R_4$ and $R_5$ is halogen and the other is CHO and $R_3$ is $C_1$-$C_4$ alkyl.

A more preferred embodiment are compounds of formula VII wherein one of $R_4$ and $R_5$ is iodine and the other is CHO and $R_3$ is $C_1$-$C_4$ alkyl.

A much more preferred embodiment are compounds of formula VII wherein one of $R_4$ and $R_5$ is iodine and the other is CHO and $R_3$ is methyl.

A preferred embodiment are compounds of formula V wherein one of $R_1$ and $R_2$ is halogen and the other is CH=CH—$CH_2$—$CH_2$—N$(CH_3)_2$ and $R_3$ is $C_1$-$C_4$ alkyl.

A more preferred embodiment are compounds of formula V wherein one of $R_1$ and $R_2$ is iodine and the other is CH=CH—$CH_2$—$CH_2$—N$(CH_3)_2$ and $R_3$ is $C_1$-$C_4$ alkyl.

A more preferred embodiment are compounds of formula V wherein one of $R_1$ and $R_2$ is iodine and the other is CH=CH—$CH_2$—$CH_2$—N$(CH_3)_2$ and $R_3$ is methyl.

A much more preferred embodiment are compounds of formula V wherein $R_1$ is iodine, $R_2$ is (E)-CH=CH—$CH_2$—$CH_2$—N$(CH_3)_2$ and $R_3$ is methyl.

A much more preferred embodiment are compounds of formula V wherein $R_1$ is (Z)-CH=CH—$CH_2$—$CH_2$—N$(CH_3)_2$, $R_2$ is iodine and $R_3$ is methyl.

Starting compounds of formula IX, X and VIII are commercially available or can be prepared by methods described in the literature. For example, a compound of formula IX, wherein $R_6$ is bromine and $R_4$ is CHO, may be prepared by the process described by Xiao-Xiang and al. in Journal of Organic Chemistry, 2000, 65, 5298. The compound of formula X, wherein $R_3$ is $C_1$-$C_4$ alkyl and $R_5$ is CHO, may be prepared by the process described in Acta Chem. Scand. 1999, 53(4), 258-262 and the compound of formula X, wherein $R_3$ is $C_1$-$C_4$ alkyl and $R_5$ is iodine, may be prepared by the process described in WO01/90105. On the other hand, compounds of formula VIII, may be prepared by the process described in J. Am. Chem. Soc 1985, 107, 217-226.

NaI is preferably used in the course of the preparation of compounds of formula VII, wherein $R_6$ is halogen, in particular Br, Cl or F.

The invention which is illustrated by the following examples is not to be understood as being limited in any way.

EXAMPLE 1

[3-Formyl-4-(2-iodo-benzyloxy)-phenyl]-acetic acid methyl ester

A solution of (3-formyl-4-hydroxy-phenyl)-acetic acid methyl ester (17.2 g, 85.9 mmol) in acetonitrile was slowly added to a solution of 1-chloromethyl-2-iodo-benzene (13.06 g, 94.5 mmol) and NaI (3.22 g, 21.5 mmol) in acetonitrile (273 ml) at reflux temperature and the mixture was mantained at this temperature for 3 hours. Once the mixture reached room temperature, the residue that had formed was filtered, washed with acetonitrile and concentrated to obtain a residue that was then dissolved in toluene (330 ml) and washed with NaOH 0.1N and water. The organic layer was concentrated to dryness, diluted with acetone (330 ml) and was stirred into water (500 ml) at room temperature. The mixture was filtered and washed with water to obtain 33.959 (96%) of [3-Formyl-4-(2-iodo-benzyloxy)-phenyl]-acetic acid methyl ester, which was purified by crystallization in toluene-cyclohexane (99% HPLC)

$^1$H-RMN (300 MHz, CDCl$_3$): 3.61 (s, 2 H, $CH_2$—$CO_2CH_3$); 3.69 (s, 3 H, $CH_3$); 5.15 (s, 2 H, O—$CH_2$-Ph); 6.99-7.92 (7H, Ar); 10.55 (s, 1 H, CHO).

EXAMPLE 2

[4-(2-Formyl-benzyloxy)-3-iodo-phenyl]-acetic acid methyl ester

2-Bromomethyl-benzaldehyde (11 g, 55.26 mmol) in acetonitrile (132 ml) was added to a solution of (4-Hydroxy-3-iodo-phenyl)-acetic acid methyl ester (16.06 g, 55 mmol), $K_2CO_3$ (8.36 g, 60.50 mmol) and NaI (2.07 g, 13.80 mmol) in acetonitrile (88 ml). The mixture was heated to reflux temperature and was stirred at this temperature for 3 hours. Once the mixture cooled down to room temperature, it was filtered and was then concentrated to dryness to obtain a residue that was diluted in toluene (212 ml) and then it was washed with NaOH 0.05N. Once the layers had separated, the aqueous layer was washed with toluene (100 ml) again and the organic layers were washed with water (2×100 ml, 1×50 ml), were concentrated to dryness to obtain a residue, which was then diluted with a mixture of acetone-water at 30° C. Then the mixture was cooled until 20-22° C. The solid formed was filtered to obtain 18 g (80%) of [4-(2-Formyl-benzyloxy)-3-iodo-phenyl]-acetic acid methyl ester (98%HPLC).

$^1$H-RMN (300 MHz, CDCl$_3$): 3.541 (s, 2H, $CH_2COOCH_3$); 3.69 (s, 3H, —$CH_3$); 5.54 (s, 2H, O—$CH_2$-Ph); 6.91 (d, J=8.4 Hz, 1H, Ar); 7.22 (dd, J=8.4 y 2.1 Hz, 1H, Ar); 7.54 (t, J=7.5 Hz, 1H, Ar); 7.69 (dt, J=7.8 Hz y 0.5 Hz, 1H); 7.73 (d, J=2.1 Hz, 1H, Ar); 7.86 (dd, J=7.8 y 1.5 Hz), 1H, Ar); 8.08 (d, J=7.8 Hz, 1H, Ar) 10.15 (s, 1H, CHO).

EXAMPLE 3

(E)-[3-(4-Dimethylamino-but-1-enyl)-4-(2-iodo-benzyloxy)-phenyl]-acetic acid methyl ester Lithium bis(trimethylsilyl)amide (LiHMDS) (1M THF, 51.5 ml, 51.5 mmol) was added drop by drop to a dispersion of (3-Dimethylamino-propyl)-triphenyl-phosphonium iodide (24.33 g, 51.2 mmol) in anhydrous toluene (300 ml) at room temperature and in an inert atmosphere. The mixture was stirred at this temperature for 1 hour. Following this a solution of and [3-Formyl-4-(2-iodo-benzyloxy)-phenyl]-acetic acid methyl ester (5 g, 12.2 mmol) in anhydrous toluene was added to the mixture and they were stirred at room temperature for 2 h 30 min. Hydrochloric acid 2N was added to the mixture and organic layers were washed by HCl 2N. Aqueous layers were washed with toluene and then they were alkalized with $K_2CO_3$. Aqueous layers were extracted with ethyl acetate, filtered, dried and concentrated to dryness to obtain 4.74 g (83%) of [3-(4-Dimethylamino-but-1-enyl)-4-(2-iodo-benzyloxy)-phenyl]-acetic acid methyl ester, which was used, without having been purified in the following step.

An analytical sample of the isomerically pure compound of the title was obtained by silica gel column chromatography from an aliquot of the reaction mixture.

(E): $^1$H-RMN (300 MHz, CDCl$_3$): 2.26 (s, 6H, N$(CH_3)_2$); 2.43 (s, 4H, $CH_2$—$CH_2$); 3.52 (s, 2H, $CH_2COOCH3$); 3.69 (s, 3H, $OCH_3$); 5.14 (s, 2H, $CH_2OPh$); 6.14 (dm, 1H, =CH—$CH_2$); 6.72 (d, J=15.6 Hz, Ph-CH=CH—); 6.83 (d, J=8.4 Hz, 1H, Ar); 7.24 (m, 3H, Ar); 7.49 (m, 2H, Ar); 7.71 (d, J=2.1 Hz, Ar).

EXAMPLE 4

(Z)-{4-[2-(4-Dimethylamino-but-1-enyl)-benzyloxy]-3-iodo-phenyl}-acetic acid methyl ester Potassium bis(trimethylsilyl)amide (KHMDS) (0.5M in toluene, 102.5 ml, 51 mmol) was slowly added to a dispersion of (3-Dimethylamino-propyl)-triphenyl-phosphonium iodide (24.3 g, 51 mmol) in anhydrous toluene (60 ml) at room temperature and in an inert atmosphere. The mixture was stirred at this temperature for 1 hour and then [4-(2-Formyl-benzyloxy)-3-iodo-phenyl]-acetic acid methyl ester (5 g, 12 mmol) in anhydrous toluene was added and was stirred at this temperature for 2 h 30 min. Hydrochloric acid 2N was added to the mixture and organic layers were washed with HCl 2N. Watery layers were washed with toluene and were alkalized with $K_2CO_3$. The aqueous layers were extracted with ethyl acetate, were filtered, dried and concentrated to dryness to obtain 10.2 g (73%) {4-[2-(4-Dimethylamino-but-1-enyl)-benzyloxy]-3-iodo-phenyl}-acetic acid methyl ester (72:28 Z/E), that was used, without having been purified in the following step.

An analytical sample of the isomerically pure compound of the title was obtained by silica gel column chromatography from an aliquot of the reaction mixture.

(Z): $^1$H-RMN (300 MHz, $CDCl_3$): 2.16 (s, 6H, $N(CH_3)_2$); 2.33 (s, 4H, $CH_2$—$CH_2$); 3.51 (s, 2H, $CH_2COOCH_3$); 3.68 (s, 3H, $OCH_3$); 5.04 (s, 2H, $CH_2O$); 5.80 (m, 1H, =CH—CH2); 6.59 (d, J=11.4 Hz, 1H, Ph-CH=CH); 6.77 (d, J=8.1 Hz, 1H, Ar); 7.24 (m, 4H, Ar); 7.64 (m, 1H, Ar); 7.70 (d, J=2.4 Hz, 1H, Ar).

EXAMPLE 5

(Z)-[11-(3-Dimethylamino-propylidene)-6,11-dihydro-dibenzo[b,e]oxepin-2-yl]-acetic acid methyl ester Method A:

A mixture of the compound of example 3 (10 g, 18 mmol), $K_2CO_3$ (7.2 g, 52 mmol) and tetrabutylammonium chloride (5.8 g, 20 mmol) in acetonitrile-water 10:1 (v/v) (400 ml) was stirred for 15 min at room temperature. Palladium acetate (II) (0.945 g, 4 mmol) was added to the previous mixture and stirred at 60° C. for 24 hours. Once the mixture cooled down to room temperature, it was concentrated to dryness, diluted in toluene (100 ml) and washed with aqueous acetic acid 10% (v/v). Aqueous-layers were washed with toluene (100 ml) alkalized with $K_2CO_3$ and then extracted with ethyl acetate, The organic layers were washed with water, were dried, filtered and concentrated to dryness thus obtaining 3.1 g of (Z)-[11-(3-Dimethylamino-propylidene)-6,11-dihydro-dibenzo[b,e]oxepin-2-yl]-acetic acid methyl ester (97.27% of purity by HPLC).

An analytical sample of the isomerically pure compound of the title was obtained by silica gel column chromatography from an aliquot of the reaction mixture.

(Z): $^1$H-RMN (300 MHz, $CDCl_3$): 2.15 (s, 6H, $N(CH_3)_2$); 2.37 (m, 4H, $CH_2$—$CH_2$); 3.52 (s, 2H, $CH_2$—$COOCH_3$); 3.67 (s, 3H, $CH_3$); 4.80 (broad, 1H, $CH_2$—O); 5.48 (broad, 1H, $CH_2$—O); 6.02 (t, 1H, =CH—$CH_2$); 6.70 (d, J=8.4 Hz, 1H, Ar); 7.02 (dd, J=8.4 y 2.4 Hz, 1H, Ar); 7.25 (mc, 5H, Ar).

Method B:

A mixture of the compound from example 4 (10 g, 21 mmol), $K_2CO_3$ (7.3 g, 53 mmol) and tetrabutylammonium chloride (5.9 g, 21 mmol) in acetonitrile-water 10:1 (v/v) (80 ml) was stirred at room temperature for 15 min. Palladium acetate (II) (0.96 g, 4.2 mmol) was added to this mixture and it was stirred at 60° C. for 24 hours. Once the mixture cooled down to room temperature, it was concentrated to dryness, diluted in ethyl acetate (160 ml), and then washed with a saturated solution of sodium bicarbonate and aqueous solution of NaCl. The organic layer was dried, filtered and concentrated to dryness to obtain 7.8 g of (Z)-[11-(3-Dimethylamino-propylidene)-6,11-dihydro-dibenzo[b,e]oxepin-2-yl]-acetic acid methyl ester (85.87% of purity by HPLC).

EXAMPLE 7

(Z)-[11-(3-Dimethylamino-propylidene)-6,11-dihydro-dibenzo[b,e]oxepin-2-yl]-acetic acid hydrochloride A mixture of the compound obtained in example 5 (method A) (1.31 g, 3.57 mmol) in methanol (25 ml) and water (5 ml) was stirred for 5 hours at room temperature in the presence of NaOH 5N (1.5 ml, 7.50 mmol). The mixture was neutralized with HCl 2N and concentrated to dryness. The product obtained was diluted with water and washed through an ionic exchange resin with a mixture of methanol-water as a mobile phase. Organic layers were concentrated to dryness to obtain 1.16 g (92%) (Z)-[11-(3-Dimethylamino-propylidene)-6,11-dihydro-dibenzo[b,e]oxepin-2-yl]-acetic acid (95% purity by HPLC).

HCl 2N (2 ml, 4.10 mmol) was added to a solution of the acid in water. The mixture was stirred and concentrated to dryness. The solution of resultant oil in acetone (25 ml) was refluxed for 30 min and the suspension obtained was cooled, filtered, washed and dried to obtain 0.88 g (70% global) of (Z)-[11-(3-Dimethylamino-propylidene)-6,11-dihydro-dibenzo[b,e]oxepin-2-yl]-acetic acid hydrochloride (99.17% of purity by HPLC).

The invention claimed is:

1. A process for the preparation of 11-[(Z)-3-(dimethylamino)propylidene]-6,11-dihydro-dibenz-[b,e]oxepin-2-yl acetic acid of formula 1 or a pharmaceutically acceptable salt thereof:

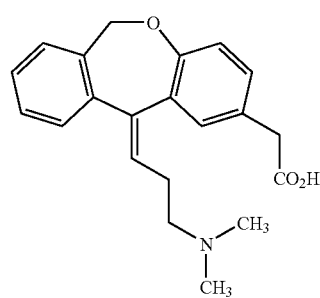

comprising reacting a compound of formula V,

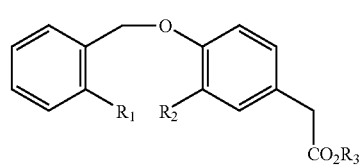

wherein one of $R_1$ and $R_2$ is halogen and the other is $CH=CH-CH_2-CH_2-N(CH_3)_2$ and $R_3$ is an acid protecting group, in the presence of a palladium catalyst, to obtain a compound of formula VI,

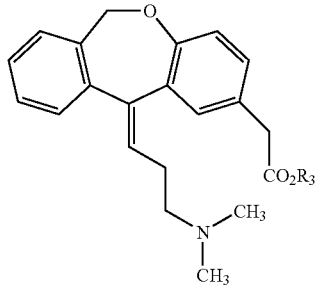

VI and removing the acid protecting group $R_3$ of said compound of formula VI to obtain the compound of formula I; and if desired, converting the compound of formula I into a pharmaceutically acceptable salt.

2. A process for the preparation of 11-[(Z)-3-(dimethylamino)propylidene]-6,11-dihydro-dibenz-[b,e]oxepin-2-yl acetic acid of formula I or a pharmaceutically acceptable salt thereof:

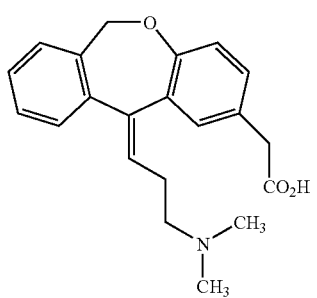

I comprising reacting a compound of formula IX

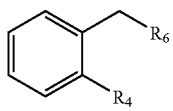

IX with a compound of formula X,

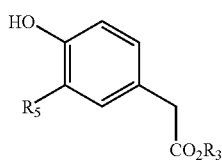

X wherein $R_6$ is a leaving group, one of $R_4$ and $R_5$ is halogen and the other is CHO and $R_3$ is as defined in claim 1, in the presence of a base to obtain a compound of formula VII,

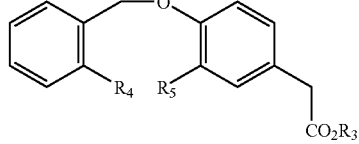

VII wherein $R_4$ is as defined for formula IX and $R_5$ and $R_3$ are as defined for formula X, reacting said compound of formula VII with a compound of formula VIII or a salt thereof,

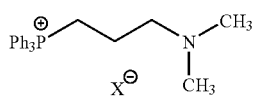

VIII wherein X is iodine, chlorine or bromine, in the presence of base to obtain a compound of formula V

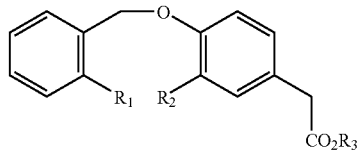

V wherein $R_1$, $R_2$ and $R_3$ are as defined in claim 1, reacting said compound of formula V in the presence of palladium catalyst to obtain a compound of formula VI

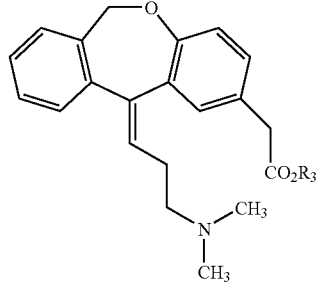

VI and removing the acid protecting group $R_3$ of said compound of formula VI to obtain the compound of formula I; and if desired, converting the compound of formula I into a pharmaceutically acceptable salt.

3. A process according to claim 1 or 2, wherein $R_3$ is $C_1$-$C_4$ alkyl.

4. A process according to claim 1 or 2, wherein the palladium catalyst is palladium acetate.

5. A process according to claim 1 or 2, wherein $R_1$ is halogen and $R_2$ is (E)-$CH=CH-CH_2-CH_2-N(CH_3)_2$.

6. A process according to claim 1 or 2, wherein $R_1$ is (Z)-$CH=CH-CH_2-CH_2-N(CH_3)_2$ and $R_2$ is halogen.

7. A process according to claim 1, wherein said compound of formula V is prepared from a compound of formula VII,

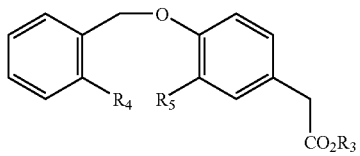

VII wherein one of $R_4$ and $R_5$ is halogen and the other is CHO and $R_3$ is an acid protecting group by reaction with a compound of formula VIII or a salt thereof.

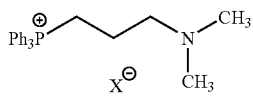

VIII wherein X is iodine, chlorine or bromine, in the presence of a base.

8. A process according to claim 7, wherein X is iodine.

9. A process according to claim 7 wherein one of $R_4$ and $R_5$ is iodine and the other is CHO.

10. A process according to claim 9, wherein $R_4$ is iodine and $R_5$ is CHO and the reaction is carried out in the presence of a lithium base.

11. A process according to claim 10, wherein lithium base is lithium bis(trimethylmethylsilyl)amide.

12. A process according to claim 9, wherein $R_4$ is CHO and $R_5$ is iodine and the reaction is carried out in the presence of a sodium base.

13. A process according to claim 12, wherein the sodium base is sodium bis(trimethylsilyl)amide.

14. A process according to claim 7 wherein said compound of formula VII is prepared from a compound of formula IX

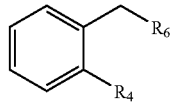

IX by reaction with a compound of formula X

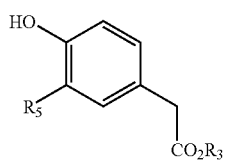

X wherein $R_6$ is a leaving group, $R_3$ is an acid protecting group and one of $R_4$ and $R_5$ is a halogen and the other is CHO in the presence of a base.

15. Process according to claim 14, wherein $R_3$ is $C_1$-$C_4$ alkyl.

16. A process according to claim 14, wherein $R_6$ is halogen.

17. Process according to claim 7, wherein $R_3$ is $C_1$-$C_4$ alkyl.

18. A process according to claim 14 or 15, wherein the base for the preparation of said compound of formula VII from said compound of formula IX is potassium carbonate.

19. Process according to claim 14, wherein the halogen is iodine.

20. Process according to claim 18, wherein the halogen is iodine.

* * * * *